United States Patent
Caprio, Jr.

[11] Patent Number: 5,925,010
[45] Date of Patent: Jul. 20, 1999

[54] THERAPEUTIC ELASTIC BODY SUPPORT

[75] Inventor: Louis Caprio, Jr., Revere, Mass.

[73] Assignee: Tru-Fit Marketing Corporation, Franklin Lakes, N.J.

[21] Appl. No.: 08/869,474

[22] Filed: Jun. 5, 1997

Related U.S. Application Data

[63] Continuation of application No. 08/538,782, Oct. 3, 1995, abandoned.

[51] Int. Cl.⁶ ..................................................... A61F 13/00
[52] U.S. Cl. ............................................... 602/62; 602/63
[58] Field of Search .................. 2/16, 22, 76; 602/62–66

[56] References Cited

U.S. PATENT DOCUMENTS

| | | | |
|---|---|---|---|
| 2,570,182 | 10/1951 | Daly et al. | 260/25 |
| 2,653,601 | 9/1953 | Morrison | 128/165 |
| 2,858,540 | 11/1958 | Morrison | 2/24 |
| 2,976,539 | 3/1961 | Brown, Jr. | 2/2 |
| 3,046,981 | 7/1962 | Biggs, Jr. et al. | 128/80 |
| 3,092,110 | 6/1963 | Duensing | 128/293 |
| 3,189,919 | 6/1965 | Chase | 2/16 |
| 3,406,406 | 10/1968 | Lutz | 2/24 |
| 3,451,232 | 6/1969 | Belzidsky | 66/171 |
| 3,600,717 | 8/1971 | McKeehan | 3/19 |
| 3,613,681 | 10/1971 | Adams | 128/293 |
| 3,677,265 | 7/1972 | Brabazon | 128/80 |
| 3,804,084 | 4/1974 | Lehman | 128/80 |
| 3,934,583 | 1/1976 | Hollingshead et al. | 602/62 |
| 3,945,046 | 3/1976 | Stromgren | 2/22 |
| 3,945,047 | 3/1976 | Jarrell, Jr. | 2/24 |
| 3,990,440 | 11/1976 | Gaylord, Jr. | 128/149 |
| 3,991,424 | 11/1976 | Prahl | 3/1 |
| 4,013,070 | 3/1977 | Harroff | 128/80 |
| 4,043,058 | 8/1977 | Hollister et al. | 36/102 |
| 4,084,584 | 4/1978 | Detty | 128/80 |
| 4,084,586 | 4/1978 | Hettick | 128/157 |
| 4,120,052 | 10/1978 | Butler | 2/16 |
| 4,150,442 | 4/1979 | Boone | 602/63 |
| 4,153,054 | 5/1979 | Boone | 128/132 |
| 4,294,240 | 10/1981 | Thill | 128/156 |
| 4,296,744 | 10/1981 | Palumbo | 128/80 |
| 4,353,362 | 10/1982 | DeMarco | 128/80 |
| 4,378,009 | 3/1983 | Rowley et al. | 128/83 |
| 4,407,276 | 10/1983 | Bledsoe | 128/80 |
| 4,423,720 | 1/1984 | Meier et al. | 128/80 |

(List continued on next page.)

FOREIGN PATENT DOCUMENTS

| | | |
|---|---|---|
| 101132 | 3/1965 | Denmark . |
| 2 622 437 | 2/1987 | France . |
| 3511250 | 7/1985 | Germany . |

OTHER PUBLICATIONS

Carol Wright Gifts, 1991 Advertisement, "Therapeutic Knee Brace".

*Primary Examiner*—Richard J. Apley
*Assistant Examiner*—Denise Pothier

[57] ABSTRACT

Elastic athletic or orthopedic supports for body parts such as the knee, thigh or ankle have a generally tubular sleeve made of an elastic "multi-directional" resilient stretch fabric that surrounds the body part. A patch having at least one lamination of neoprene or the like is attached within the sleeve. The patch is sized, shaped and positioned on the support element to provide a therapeutic warming to only a portion of the body part. Preferably the patch includes the second lamination of an absorbent fabric liner that is coextensive with, and secured to, the neoprene layer. The neoprene layer has a plurality of holes that extend through it to remove moisture. The liner can have like aligned holes. The liner and the patch are sewn, edge-sewn, adhered, heat-laminated, or otherwise attached to one another and to the sleeve. For a knee or elbow, the patch is generally diamond shape with its wide ends truncated and the elastic sleeve may have an opening at the rear of the knee or the inside of the elbow. For a wrist, ankle or thigh, the patch is generally a strip that wraps or extends over the injured region, with openings in the wrist and ankle sleeves for the thumb and heel, respectively. For an ankle, the strip curves downwardly at its ends to cover the ankle bone directly.

10 Claims, 13 Drawing Sheets

U.S. PATENT DOCUMENTS

| | | | |
|---|---|---|---|
| 4,470,411 | 9/1984 | Hoyt, Jr. | 128/165 |
| 4,516,572 | 5/1985 | Schlein | 128/156 |
| 4,651,722 | 3/1987 | Karczewski | 128/80 |
| 4,724,831 | 2/1988 | Huntjens | 128/80 |
| 4,765,318 | 8/1988 | Tranberg et al. | 128/80 |
| 4,832,010 | 5/1989 | Lerman | 128/165 |
| 4,964,402 | 10/1990 | Grim et al. | 128/80 |
| 5,014,354 | 5/1991 | Dumont | 2/23 |
| 5,020,164 | 6/1991 | Edwards | 2/239 |
| 5,024,216 | 6/1991 | Shiono | 128/80 |
| 5,086,761 | 2/1992 | Ingram | 602/269 |
| 5,136,727 | 8/1992 | Brisco | 2/409 |
| 5,139,476 | 8/1992 | Peters | 602/26 |
| 5,168,577 | 12/1992 | Detty | 2/16 |
| 5,221,252 | 6/1993 | Caprio et al. | 602/63 |
| 5,306,229 | 4/1994 | Bradt et al. | 602/26 |
| 5,382,223 | 1/1995 | Springs | 602/6 |
| 5,383,843 | 1/1995 | Watson et al. | 602/13 |
| 5,417,646 | 5/1995 | Gauvry | 602/26 |
| 5,449,341 | 9/1995 | Harris | 602/63 |
| 5,474,524 | 12/1995 | Carey | 602/62 X |

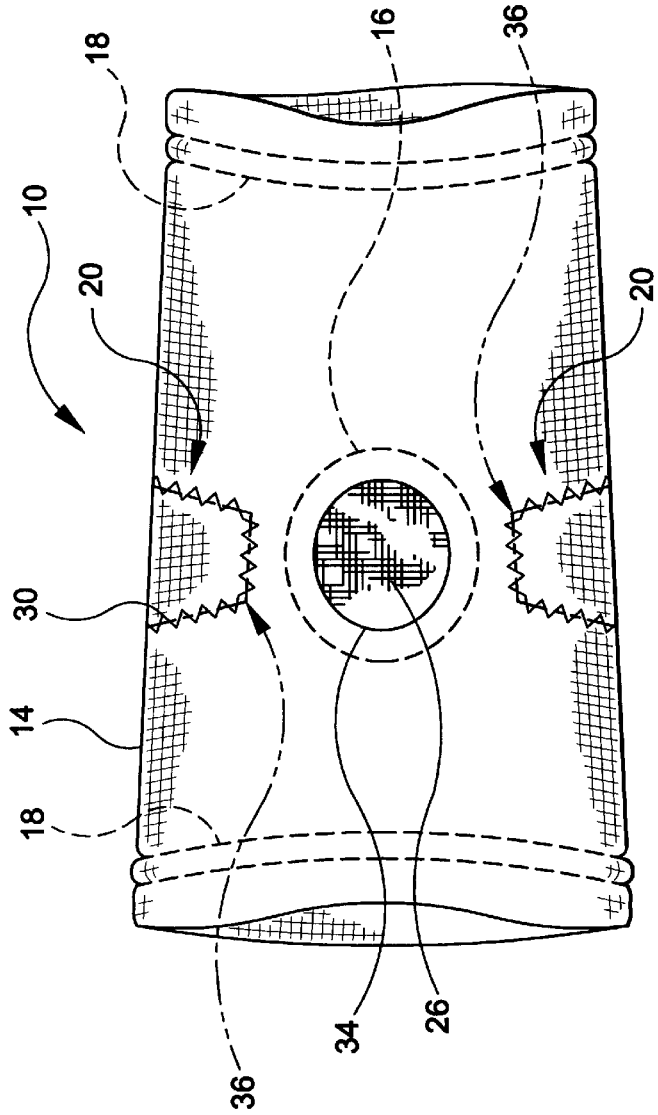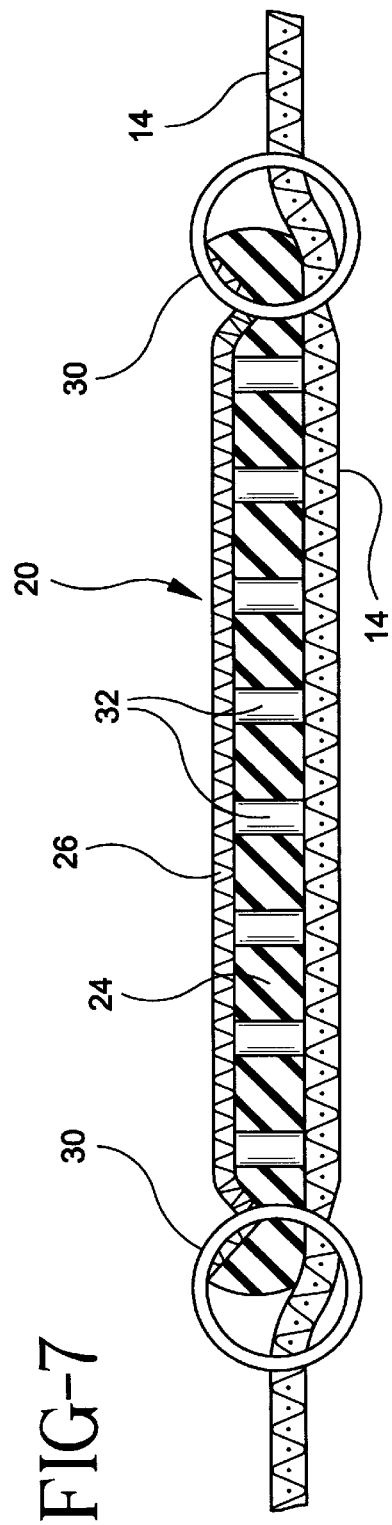
FIG-6
FIG-7

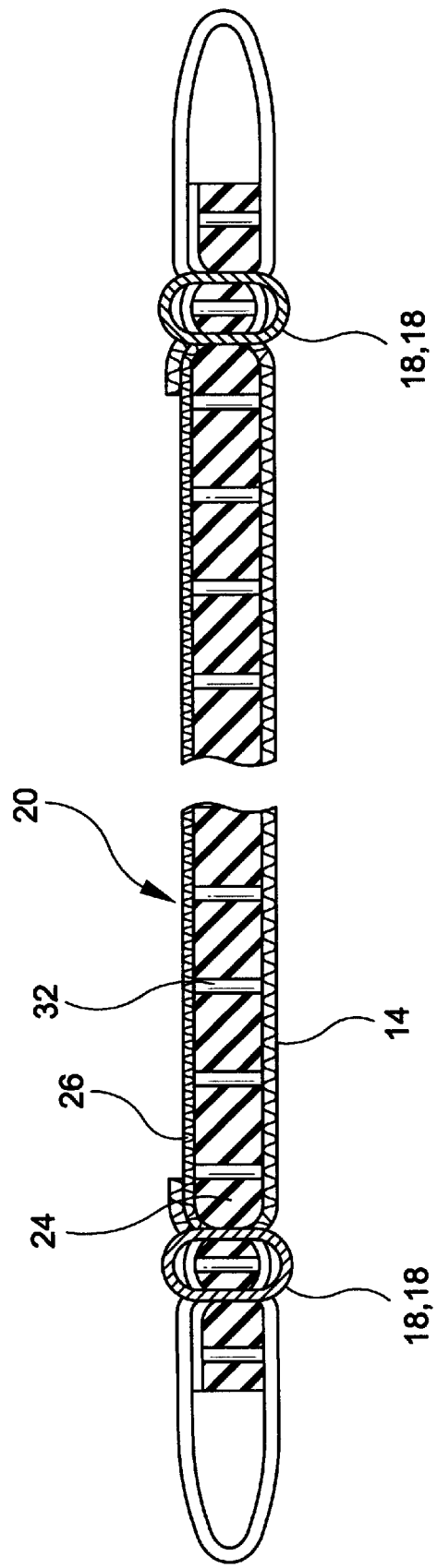

THERAPEUTIC ELASTIC BODY SUPPORT

This is a continuation of application Ser. No. 08/538,782 filed on Oct. 3, 1995, now abandoned.

BACKGROUND OF THE INVENTION

This invention relates in general to elastic athletic and orthopedic supports for the human body. More specifically, it relates to an improved support which provides a therapeutic degree of heating only to a strategically placed portion of a body region, and does so without an unacceptable level of perspiration build-up, overheating, or chafing due to fabric rub or bite.

A wide variety of externally applied elastic supports and rigid, joint-immobilizing braces are known to protect healthy and injured joints and to promote healing of certain injuries. Supports and braces are commonly used for injuries and other medical problems at the knee, thighs, elbow, waist, wrist and back. Common injuries that can be helped by a support include strained or torn ligaments, tendinitis, arthritis, and pulled or strained muscles.

Elastic or "soft" supports are usually preferred over braces where the body part is generally healthy and the intent is to support it in order to prevent injury e.g. of a joint and surrounding tissue. Soft supports are also used to protect and promote the healing of injured members where there are no broken bones and the patient is mobile. A support may be worn, for example, before engaging in work or a sports activity that is expected to involve unusual stretching or load bearing. The elasticity of the support is important not only to apply a supporting externally applied compression, but also to maintain the support in a selected position on the body. Ideally the a support in constructed so that in flexes easily and interferes as little as possible with the normal range of motion of the body part. The elasticity of the support also accommodates change in the size of the body part produced by physical exertion, changes in the condition of an injury (e.g., a reduction in swelling), or mere changes in the elevation of the body part, e.g., when an injured ankle is elevated.

The most common form of elas tic support-is a simple tubular sleeve of a stretch fabric such as the stretch nylon material used in Ace® brand bandages and supports. The sleeve is pulled over and grips the body part to be protected as well as adjoining regions. When used on joints, a major problems are the chafing and bite of the fabric during flexure, particularly at the interior of a joint such as the back of a knee or the "inside" of a elbow. Flexures of body parts and changes in body size can also result in a migration of the position of the support on the body.

To overcome some of those problems, it is also known to construct flat or "unfolding type" supports which wrap around the body part and are secured with straps with hook-and-loop or other fasteners. U.S. Pat. Nos. 4,353,362 to Demarco and U.S. Pat. No. 5,221,252 to the present applicant and another are examples of such supports for knees.

It is also known to combine the support function of these devices with therapeutic heating or cooling functions and protective padding functions. U.S. Pat. No. 5,014,354 to Dumont, for example, uses pads secured to a main elastic body to protect the underlying body portion against falls or other impacts. U.S. Pat. No. 5,168,577 to Detty discloses the use of a continuous layer of neoprene in the material forming the main elastic body where the neoprene acts as an insulator to retain body heat, and thereby increase blood flow to the area. U.S. Pat. No. 5,136,727 to Brisco describes a pair of athletic shorts formed from a pair of conventional ventilated fabric briefs attached to neoprene legs that surround the thighs of the wearer. U.S. Pat. No. 4,964,402 to Grin et al. is illustrative of another approach, the use of pockets formed in the main elastic body where the pockets are adapted to hold hot or cold packets and thereby heat or cool the body region under the pack.

Pockets and thermal packs are not in wide use. They require that packs be heated, cooled or activated, and then supplied to the support for immediate use. These pack heat or cool only for a limited period of time. They must then be removed and replenished or replaced, which typically requires removing the entire support and "reloading" the pockets. The packs are also bulky and they present a significant cost increase as compound to conventional soft supports, and even soft supports with neoprene linings.

A major problem with neoprene and other closed-cell, heat-retaining materials is that they trap perspiration and excessive heat under the support. Trapped moisture and high heat levels quickly produce discomfort and chafing. Moisture also promotes migration because it lubricates the support-skin interface. Such devices cannot be used for extended periods of time, e.g. usually not more than a few hours at the maximum. Another problem is that the neoprene adds to the weight and resistance to flexure of the support as well as promoting chafing and bite. Unless that are enclosed or otherwise protected, neoprene and like products are also susceptible to edge fraying, that is, a ripping and/or crumbling away of the material at its edges.

U.S. Pat. No. 4,832,010 to Lerman discloses a soft support formed from three layer laminate material of neoprene sandwiched between and adhered to two layers of a stretch fabric. The neoprene therefore extends throughout the support. The resilient strength of the neoprene layer is an important source of the supporting compression force. Lerman uses holes that extend only through the neoprene layer to allow an air flow to the body part that removes perspiration and excess heat. Because the holes weaken the neoprene, Lerman teaches that the neoprene must be dense and that the two stretch fabric layers must both be adhered to the neoprene so that their inherent resilience can supplement the compressive force of the neoprene.

Other perforated, closed-cell laminates are known. Cushion sole inserts long for shoes, for example, have a layer of a closed cell foam sandwiched between fabric layers with air holes extending through all three layers.

It is therefore a principal object of this invention to provide an elastic support for a body part, particularly a joint, which also provides a strategically placed therapeutic heating without thermal packs or other external sources of thermal energy.

Another object is to provide the foregoing advantages which also control the build up of moisture at the heated portion of the body part and control chafing and bite, especially during joint flexure.

A further advantage of the present invention is to provide a support with the foregoing advantages which is highly flexible and operate effectively over a range of sizes of the body part.

Still another advantage of the present invention is to provide the foregoing advantages without any significant increase in bulk over a simple elastic sleeve support.

A further object of this invention is to provide all of the foregoing advantages while retaining a favorable cost of manufacture.

SUMMARY OF THE INVENTION

An elastic support for a body part, particularly a joint such as the ankle, elbow, wrist or knee, has a main elastic member formed of a multi-directional stretch fabric which, when positioned over the body part, surrounds the body part in a stretched condition to develop a compressive supporting force. The main elastic member is preferably a tubular sleeve of a two, three, or four way stretch nylon that is pulled over the body part.

The sleeve carries a patch or panel with at least one layer formed from a flexible sheet of a heat-retaining material such as a closed-cell foam. Neoprene is preferred. The patch preferably also has a stretch fabric liner that is generally coextensive with the heat-retaining layer and disposed between that layer and the body part. The liner is preferably formed of a fabric such as stretch nylon or a polypropylene which wicks moisture (perspiration) and controls chafing due to repeated relative movements of the liner with respect to the body part. To control a build up of moisture under the heat-retaining layer, it has a plurality of small diameter holes formed in it which extend between its faces. The liner may have a like pattern of holes aligned with those in the heat-retaining layer to facilitate a circulation of air through the patch to remove excess moisture. The patch can include a second fabric layer to sandwich the heat-retaining layer, but it is not necessary.

The liner is secured to the patch to maintain then in an overlapping, mutually aligned relationship despite manipulation during manufacture and shear forces during use. The patch, in turn, is secured to the main elastic sleeve at a selected location over the body part to be therapeutically treated. Both of these securing can be by (i) edge stitching, (ii) spot gluing and edge stitching, (iii) other stitching, (iv) adhesion, (v) heat lamination, (vi) hook-and-loop materials, or (vii) combinations of the foregoing.

For knees and elbows, the patch is preferably generally diamond shaped, centered over the knee cap or elbow, and sized to cover the knee cap or elbow and adjacent soft tissue. For ankles and wrists the patch is a strip that partially circles the wrist or the ankle joint. For ankles, the ends of the strip preferably curve downwardly to cover the protruding ankle bone. For thighs the patch is a strip that extends vertically over a muscle group in the thigh to be treated, e.g. a hamstring muscle. For knees and elbows, the main elastic sleeve preferably has an interior opening at the rear of the joint to avoid fabric bite during a flexure of the joint. For ankles and wrists, the main elastic sleeve preferably has an interior opening sized and positioned to receive the heel and thumb, respectively.

These and other object and features will be more readily understood from the following detailed description which should be read in light of the accompanying drawings.

BRIEF DESCRIPTION OF THE DRAWINGS

FIGS. 4–6 are perspective and front and rear flattened plan views, respectively, of an elastic knee support accordingly to the present invention with portions of the perspective and front plan views broken away;

FIG. 7 is a view in section taken along the line 7—7 in FIG. 5;

FIG. 19 is a view in section taken along the line 19—19 in FIG. 17.

DETAILED DESCRIPTION OF THE PREFERRED EMBODIMENTS

Figure 1:
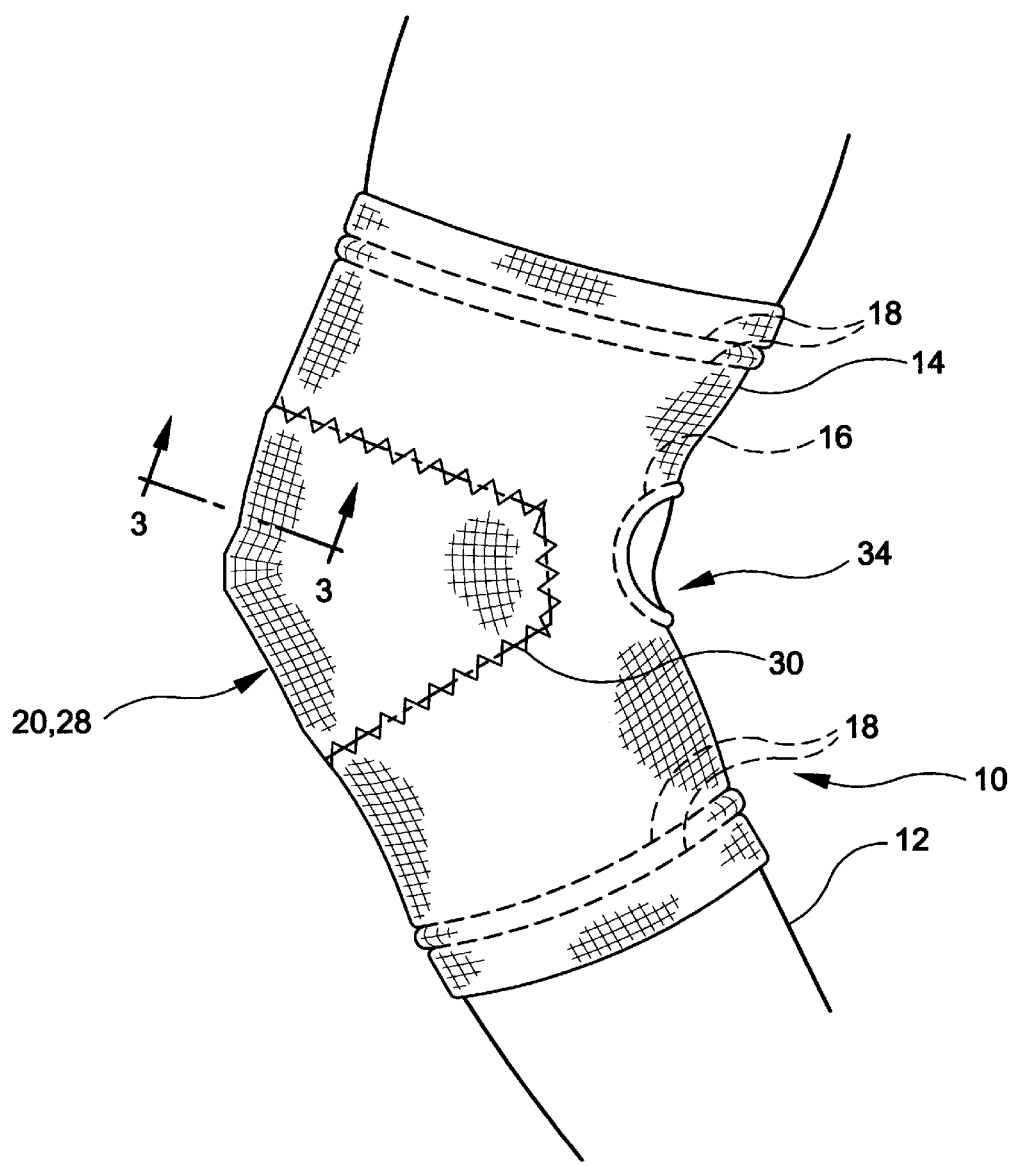
FIGS. 1 and 2 are perspective and outer flattened plan views, respectively, of an elastic elbow support according to the present invention with portions of the plan view broken away.

FIGS. 1–19 show elastic supports 10 according to the present invention adapted for use on human body parts including the elbow, knee, ankle, wrist and thigh. In each of these forms, the support 10 is constructed about a generally tubular or sleeve-like main support member 14. For ease of reference, the member 12 may be referred to herein as a "sleeve", but it will be understood that the sleeve may have openings and may be an "unfolded" type of support that is wrapped around the body part and secured by fasteners or straps and fasteners.

The sleeve 14 is formed of a multi-directional, resilient, stretch material such as a two, three or four-way stretch nylon, and preferably the woven two way stretch nylon material commonly used in ACE® brand bandages and conventional sleeve-type supports. The direction of stretch is oriented to allow the sleeve to expand radially about the body part, but to resist stretching along the body part, e.g., vertically along the leg or along the central axis of the arm. As shown, end openings and other openings in the sleeve 14 are turned under and stitched, as at 16, or double stitched, as at 18, 18, to avoid end fraying and provide a smooth edge at the openings to facilitate sliding the support onto and off the body part. The sleeve 14 is the principal source of compressive force in the elastic support 10 constructed according to the present invention. It is sized so that when it is drawn over the associated body part it is placed in a stretched condition. Its inherent resiliency produces a compressive force that surrounds and supports the body part. The sleeve is porous to air.

The compressive force generated by the sleeve should be sufficient to provide therapeutic support for the body part and to hold the support in place despite flexures of joints and changes in body size due to changes in blood flow, blood pressure, swelling, or edema. It should also produce the desired force levels or a reasonable range of sizes of the body parts so that most adults can be accommodated by one of four pre-set sizes, as is standard for conventional sleeve-type supports currently on the market.

A principal feature of the present invention is a panel or patch 20 attached to the sleeve 14. The patch is a laminate construction having at least one layer 24 of a flexible heat-retaining material such as a closed-cell foam, and preferably neoprene. In the preferred form shown in FIGS. 1–19, the patch also includes a liner 26 that is generally co-extensive with the heat-retaining layer 24. The liner is a stretch fabric that can wick moisture, and preferably is a woven, four-way stretch nylon. The liner is also soft to control chafing of the body part. It also protects the heat-retaining layer against mechanical degradation, particularly at the edges.

As will be described in more detail below, the patch is sized, shaped and located on the sleeve so that is overlies only a portion 28 of the body part 12 which requires heat therapy or protection (the heat being supplemental to the support therapy of the elastic sleeve). For example, for a knee support, the patch may cover only the patella (knee cap) and its immediately surrounding tissue. The patch thus focuses its therapeutic heating action on the injured or vulnerable portions of the body part. This allows the rest of the body part to expand and contract more freely then it would if completely surrounded by a neoprene layer and to "breath" directly through the sleeve 14. This in turn increases the comfort of the support 10 and increases the period of time that it can be worn comfortably and provide heat therapeutic benefits to the body portion 28. These therapeutic benefits include (i) increasing the blood supply to an injury such as sprained or torn ligament or muscle, or medical problem such as arthritis or tendinitis, (ii) treating conditions such as swelling, and edema, and (iii) providing a mechanical protection (padding) against injury or aggravation of an existing injury or condition due to an externally applied blow.

The liner 26 does not need to be continuously bonded to the neoprene layer 24, although it may be. It is sufficient that the liner be held in a fixed position interposed between the layer 24 and the body portion 28. To facilitate manufacture, it is preferred that the liner 26 is secured to the layer 24, whether temporarily or permanently, and then the laminated double layer patch is permanently secured to the sleeve, preferably at its inner surface. The precise method of attachment of lamination of the patch layer and of its patch to the sleeve is not critical. It can be a continuous adhering, a sewing, an edge-sewing, heat lamination, spot gluing and sewing (especially edge-sewing), hook-and-loop materials such as VELCRO®, and combinations of these techniques. The presently preferred method is to spot glue the liner to the neoprene layer to hold then in the desired assembled condition, and then edge-stitch the assembled and tacked-together patch to the sleeve, which simultaneously stitches the liner to the heat-retaining layer. Edge stitching 30 is shown in FIGS. 1–19. It serves both to secure the elements 14, 24, and 26 to one another and, in combination with the liner 26, to protect the edges of the layer 24 from fraying or other mechanical abuse such as rips and gouges.

The layer 24 has a plurality of openings 32 that extend through the layer 24, from one face to the other. As shown, they are cylindrical. The size and spacing of the holes is sufficient to produce a circulation of air through the porous fabric liner 26 to body portion 28 which promotes an effective evaporation of perspiration. In the illustrated support, using 1/8 inch thick neoprene, the holes are about 1/16 inch in diameter and spaced uniformly with about 1/4 inch spacing between holes, center to center.

The openings 32 work in cooperation with the liner 26 which, because it is woven, porous, and produces a capillary or wicking action for moisture that has accumulated under the layer 24, transports air and moisture to the openings 32. In the presently preferred form, at least for the elbow, ankle and wrist, the liner 26 also has a set of internal openings 33 that are aligned with the holes 32 in the heat-retaining layer. The openings 33 increase the evaporative action since portions of the body directly under the holes 33 have direct access to the air passages 32, and there is an increased flow accessibility between the rest of the liner 26 and the holes 32. The holes 32 and 33 are produced by any known technique for such materials such as punching or drilling.

When used on a joint, a tubular sleeve is prone to a buckling of the sleeve fabric at the interior of the joint when it bends. Adjacent folds of the fabric can pinch or "bite" the skin at the "back" of the joint. There is also an enhanced chafing due to a rubbing of the folded sleeve material which is pressed against and moves over the skin at in joint during the bending. To reduce chafing and bite, in its presently preferred form the invention utilizes comparatively large internal openings 34 in the sleeve. The openings are located over the inner, central portion of the joint. They are sized and shaped so that there is substantially no bite over the normal range of notion for that joint. As shown, the presently preferred form for the openings 34 is oval or circular, depending on which body part is being treated.

Figure 2:
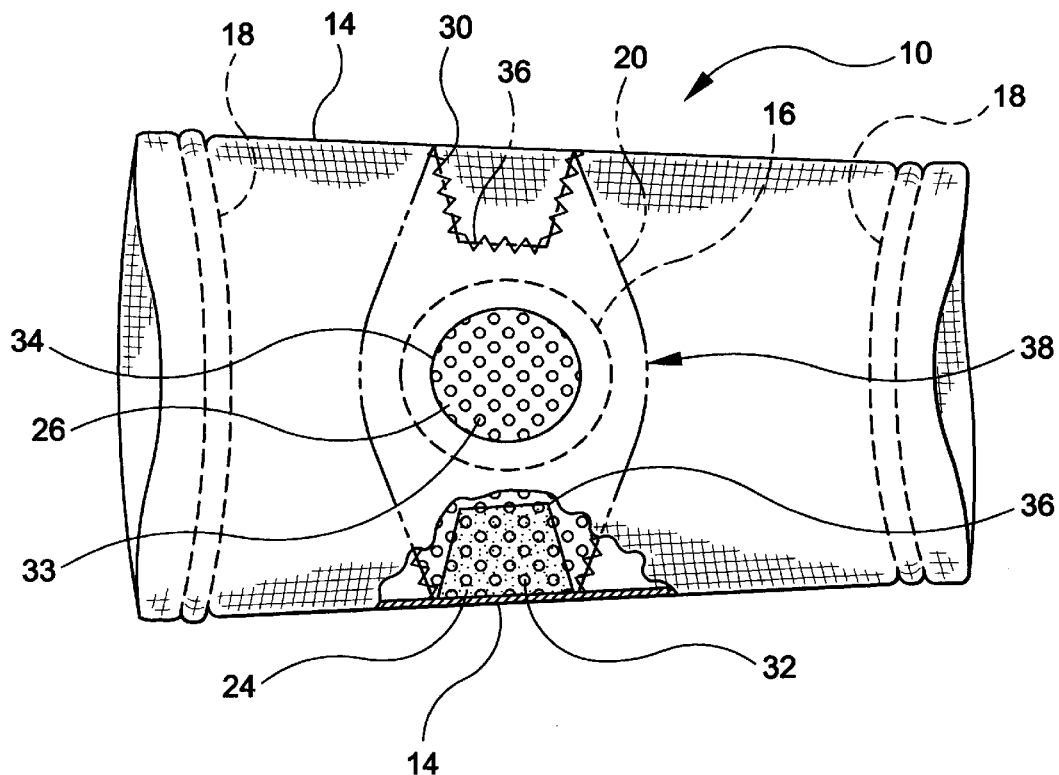
Figure 3:
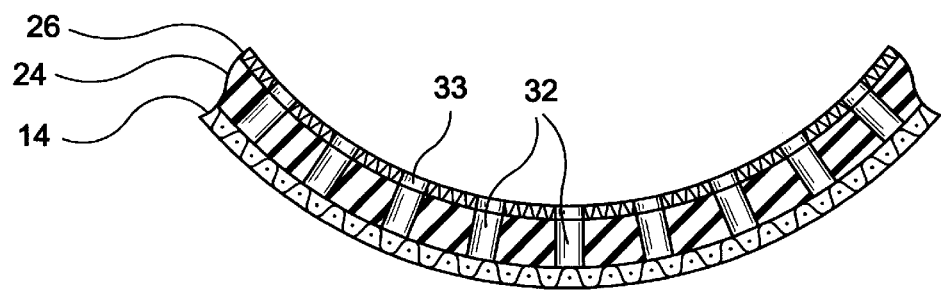
FIG. 3 is a view in sectional taken along the line 3—3 in FIG. 2.
Figure 4:
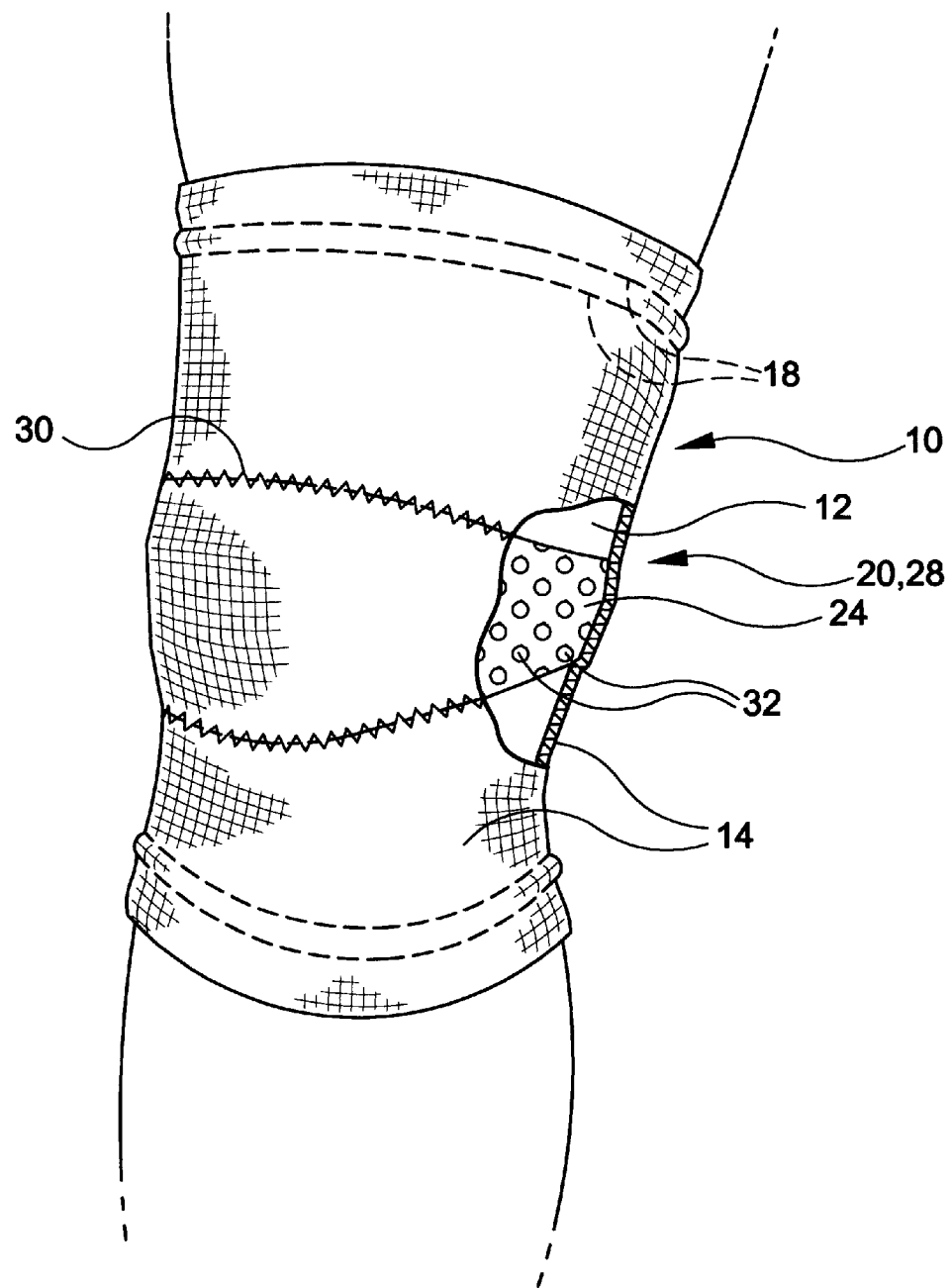
Figure 5:
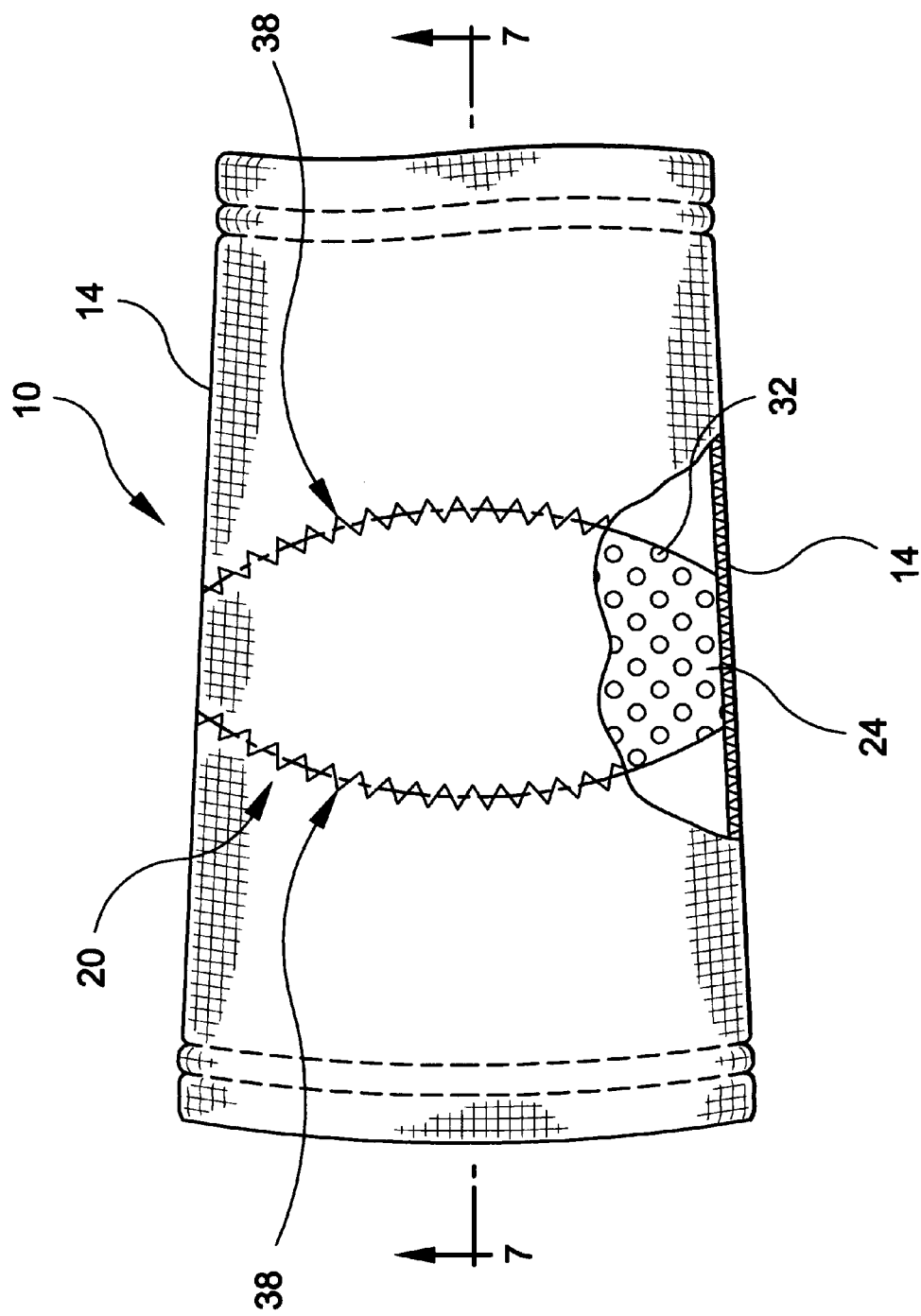
Figure 8:
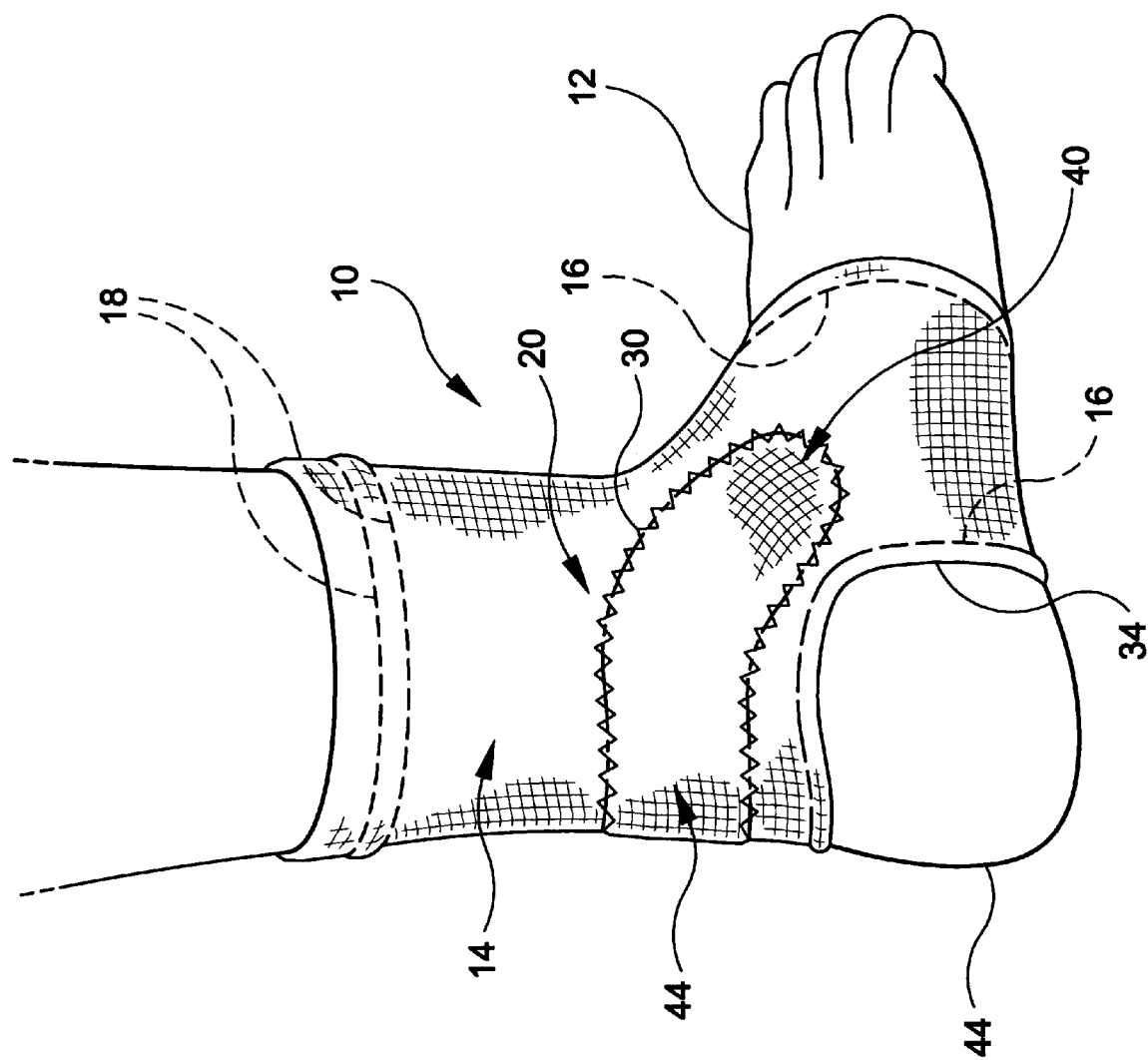
FIGS. 8–11 are views in perspective, and flattened front, rear and side elevations, respectively, of an elastic ankle support according to the present invention.
Figure 10:
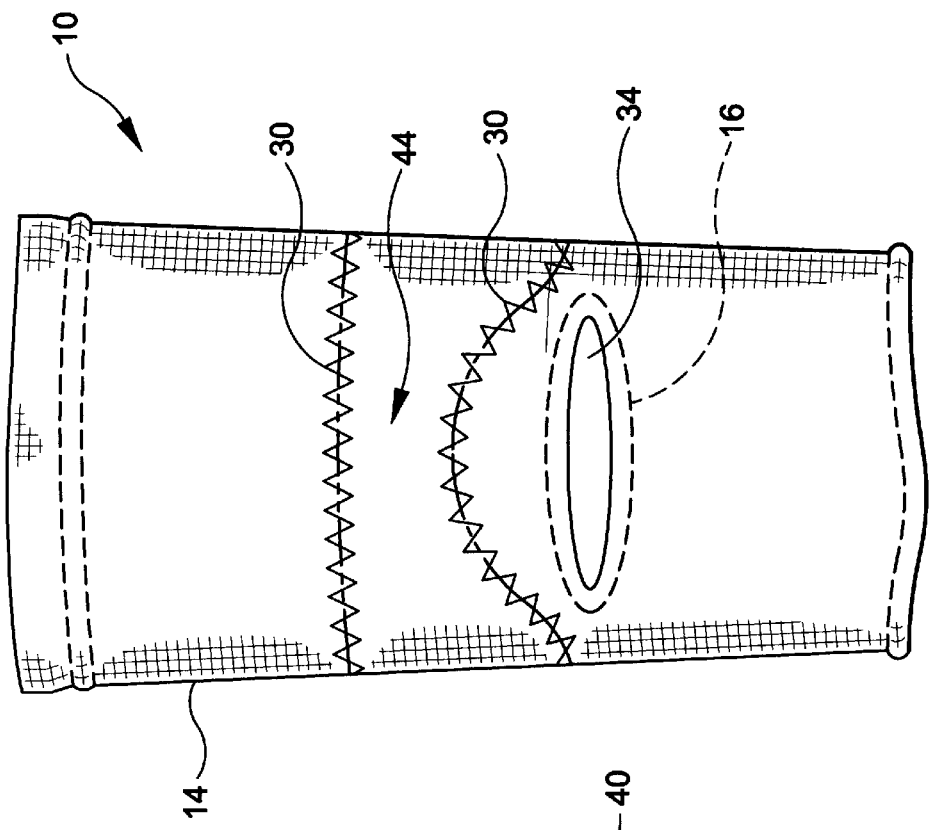
Figure 9:
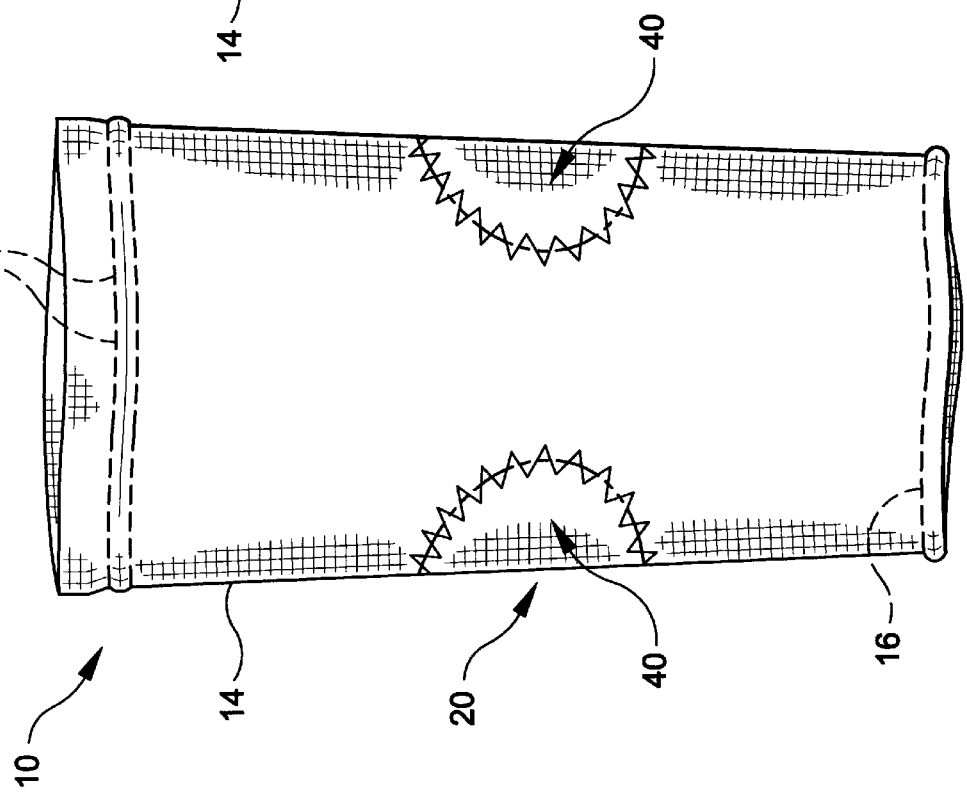
Figure 11:
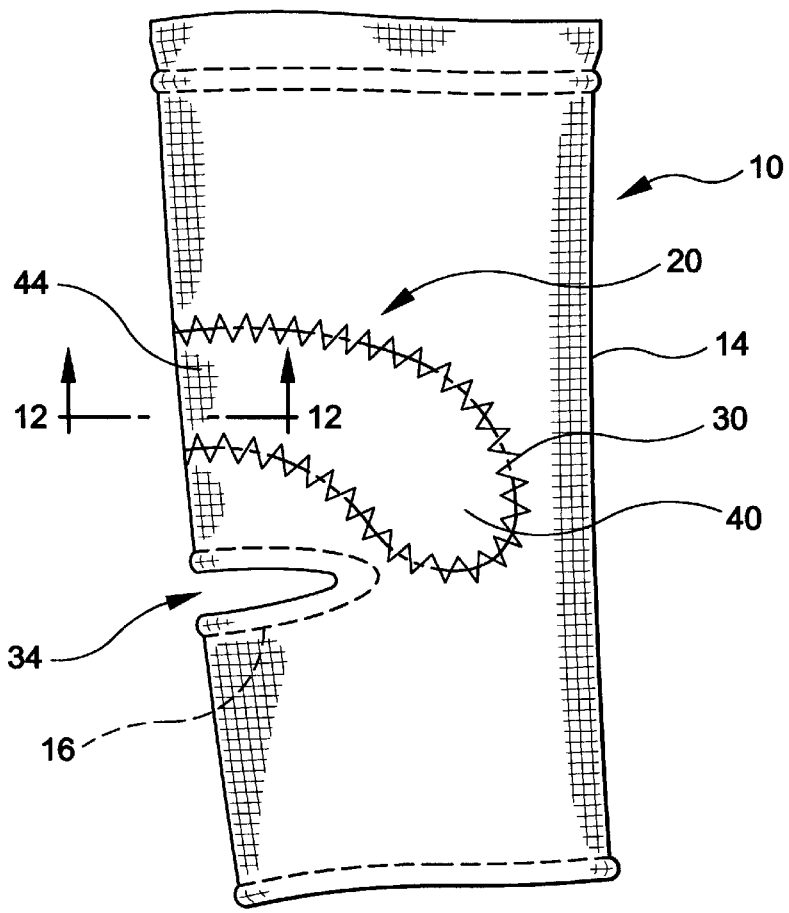

FIGS. 1–3 show a support 10 particularly adapted for use on an elbow. As shown, the support is positioned with the patch 20 covering the protruding elbow bone and adjacent tissue. As best seen in FIG. 2, the patch is in the general shape of a diamond but with the two laterally extending ends 36,36 truncated. The shape can also be viewed as a "puckered" or middle-bulging strip. The patch extends along the arm, between rounded corners 38, 38, and along the lateral direction between ends 36, 36, for sufficient distances that the region of the body needing treatment is covered, and remains covered, throughout flexures of the elbow. The patch is spot glued and edge-stitched. It has a layer 24 of 1/8 inch thick neoprene and a four way stretch nylon liner 26. Holes 32 and 33 in the patch are aligned. When unstretched, the opening 34 is slightly oval with the major axis directed along the arm to accommodate a fairly large angular travel of the forearm with respect to the upper arm.

FIGS. 4–7 show a support 10 adapted for use on a knee. The patch 20 is again generally diamond shaped with truncated ends 36, 36 and rounded ends 38, 38. Again, the shape can be viewed as a "puckered" or middle-bulging strip. The centered widening ensures coverage of the knee cap and vertically adjacent tissue by the layer 24 even when the knee is fully flexed. The inherent elasticity of the sleeve 14, layer 24, and liner 26 facilitate a flexure of the knee while maintaining the therapeutic patch coverage. The patch is preferably spot glued and edge-stitched at 30. It has an opening 34 at the rear of the knee to control bite and chafing there. The opening 34 is generally circular when it is not stretched, as shown in FIG. 6. The sleeve 14 narrows from top to bottom to accommodate variations in the size of the thigh and calf. As is best seen in FIG. 7, the liner 26 is preferably a stretch fabric with no openings 33 since the knee cap is typically more prone to irritation due to a chafing arising from a sliding of the liner over the knee cap than to a build up of perspiration. Note that because the patch is interrupted by the opening 34, it does not encircle and cannot itself generate any significant level of compressive force on the knee. The present invention thus decouples the support and therapy functions which are inherently combined in conventional supports with continuous, body-surrounding neoprene layers. FIG. 7 also demonstrates visually that the layer 24 can also serve a padding function.

Figure 12:
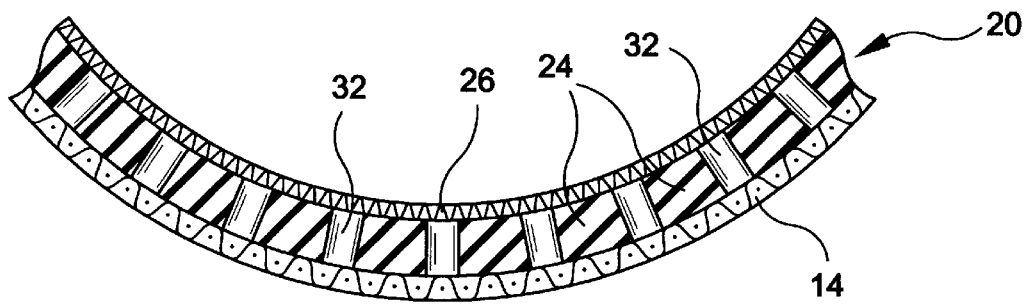
FIG. 12 is a view in section taken along the line 12—12 in FIG. 11.
Figure 13:
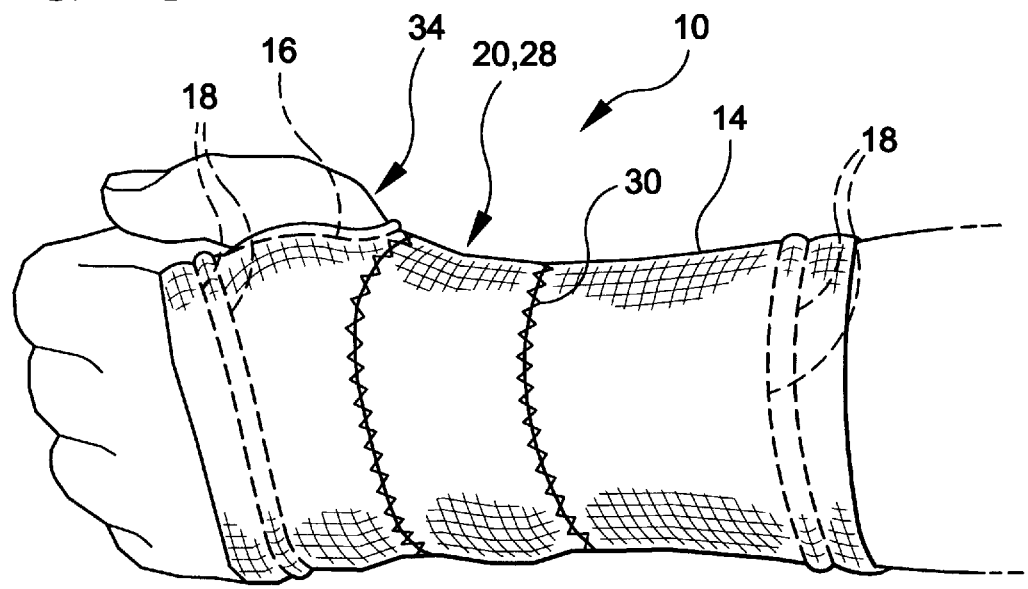
FIGS. 13–15 are views in perspective, outer flattened plan, and inner flattened plan, respectively, of an elastic wrist support according to the present invention.
Figure 14:
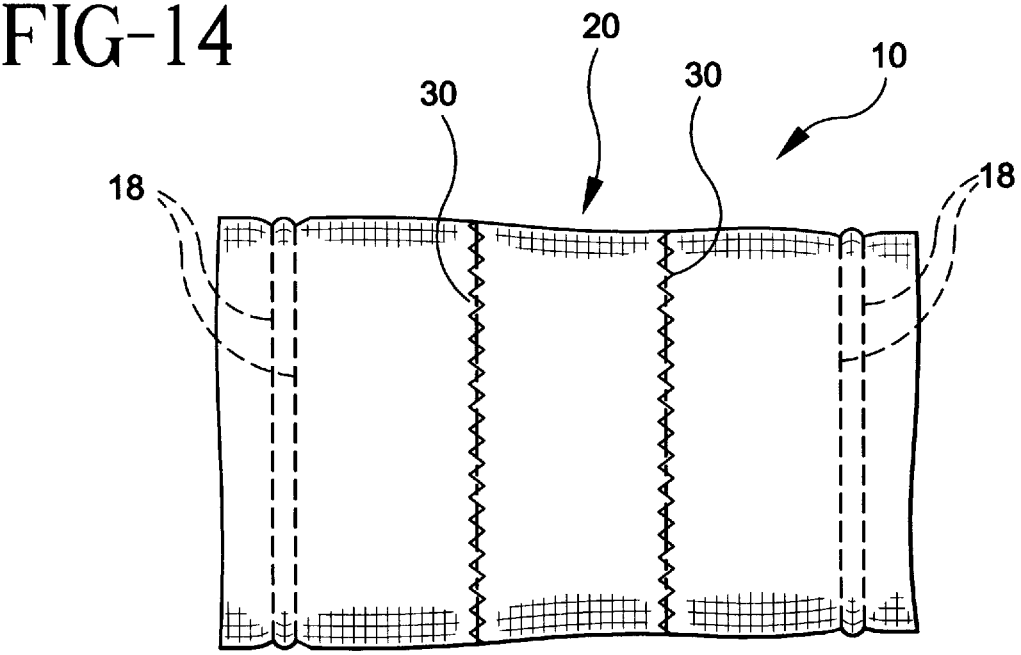
Figure 15:
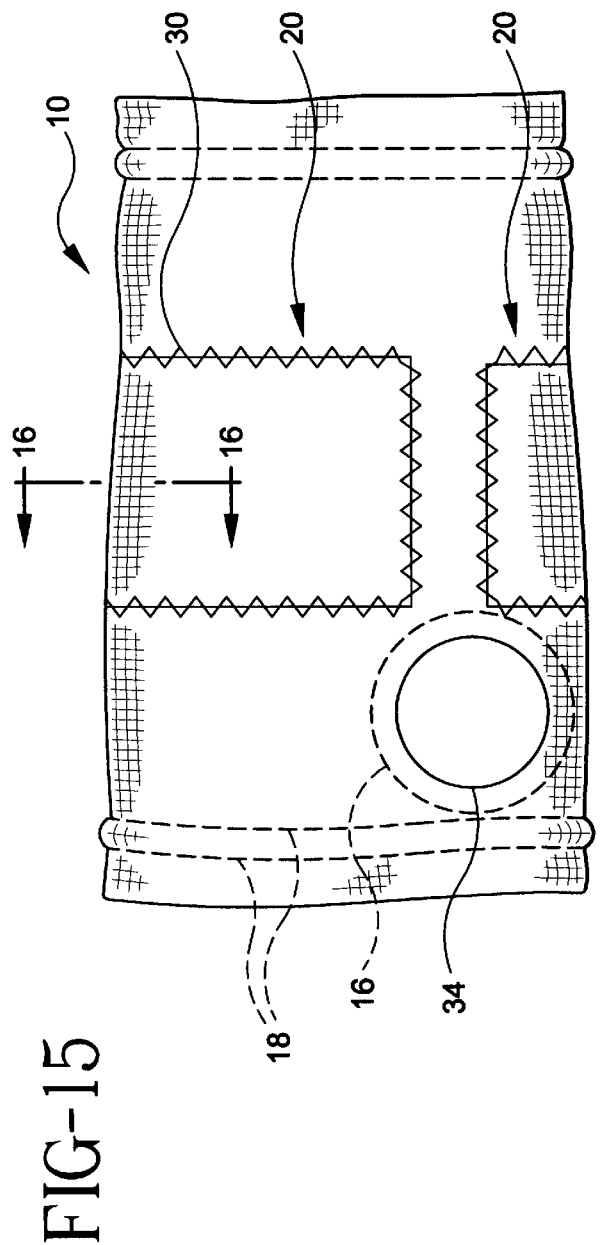
Figure 16:
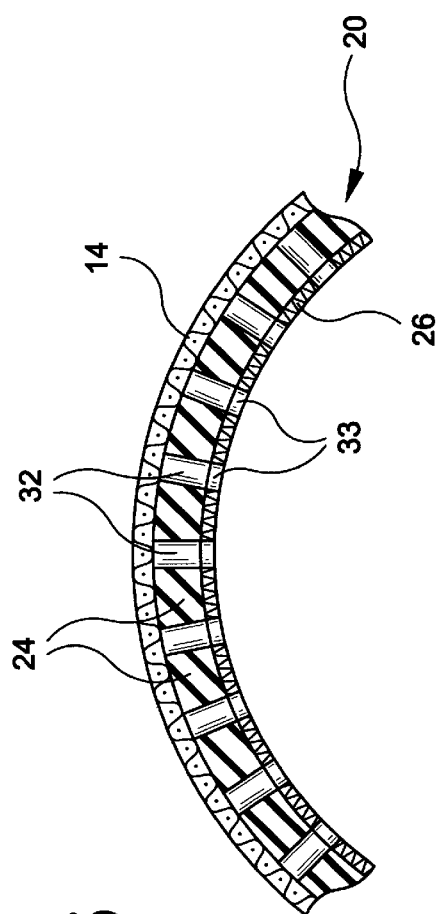
FIG. 16 is a view in section taken along the line 16—16 in FIG. 15.

FIGS. 8–12 shows a support 10 adapted for use on an ankle. The patch 20 is more on the form of a laterally extending strip with downwardly curved, rounded ends 40,40 positioned to overlie the laterally protruding ankle bone at both sides of the ankle. A central portion 42 of the patch extends around the back of the ankle to cover the Achilles tendon region above the heel 44. The patch 20 thus covers, and can provide therapy to, the ankle joint and a major tendon group. At the same time it supports the rest of the ankle joint and adjacent portions of the foot without overheating and without any significant increase in bulk as compared to such a support formed entirely with a layer of a heat-retaining material, e.g., a support made entirely of Lerman-type laminate as described in U.S. Pat. No. 4,832,010. The opening 34 for an ankle is a relatively flat oval, or slitlike, when not stretched. It receives the heel and facilitates the initially straight tubular sleeve 14 in assuming a generally L-shaped orientation when worn. It also allows the sleeve 14 to be woven with less fabric at the front of the support, opposite the heel, to reduce folding, biting and chafing. The sleeve tapers slightly from top to bottom to reflect the usually larger diameter of the lower leg as compared to the middle of the foot. As shown in FIG. 12, the liner 26 preferably has holes 33.

FIGS. 13–16 show a support 10 adapted for use as a wrist support. The sleeve 14 has a slight taper, narrowing toward the hand, and a thumb-receiving opening 34 positioned at the upper "side" of the support. The patch 20 is a generally parallel-edged strip which encloses most of the wrist, as shown. The patch is again spot glued and edge stitched to the inner surface of the sleeve. The wrist can generate significant perspiration, and therefore the liner 26 is perforated with the holes 33. The support 10 provides mechanical support to the wrist and adjacent parts, but provides heat therapy focused only on the wrist joint itself.

Figure 17:
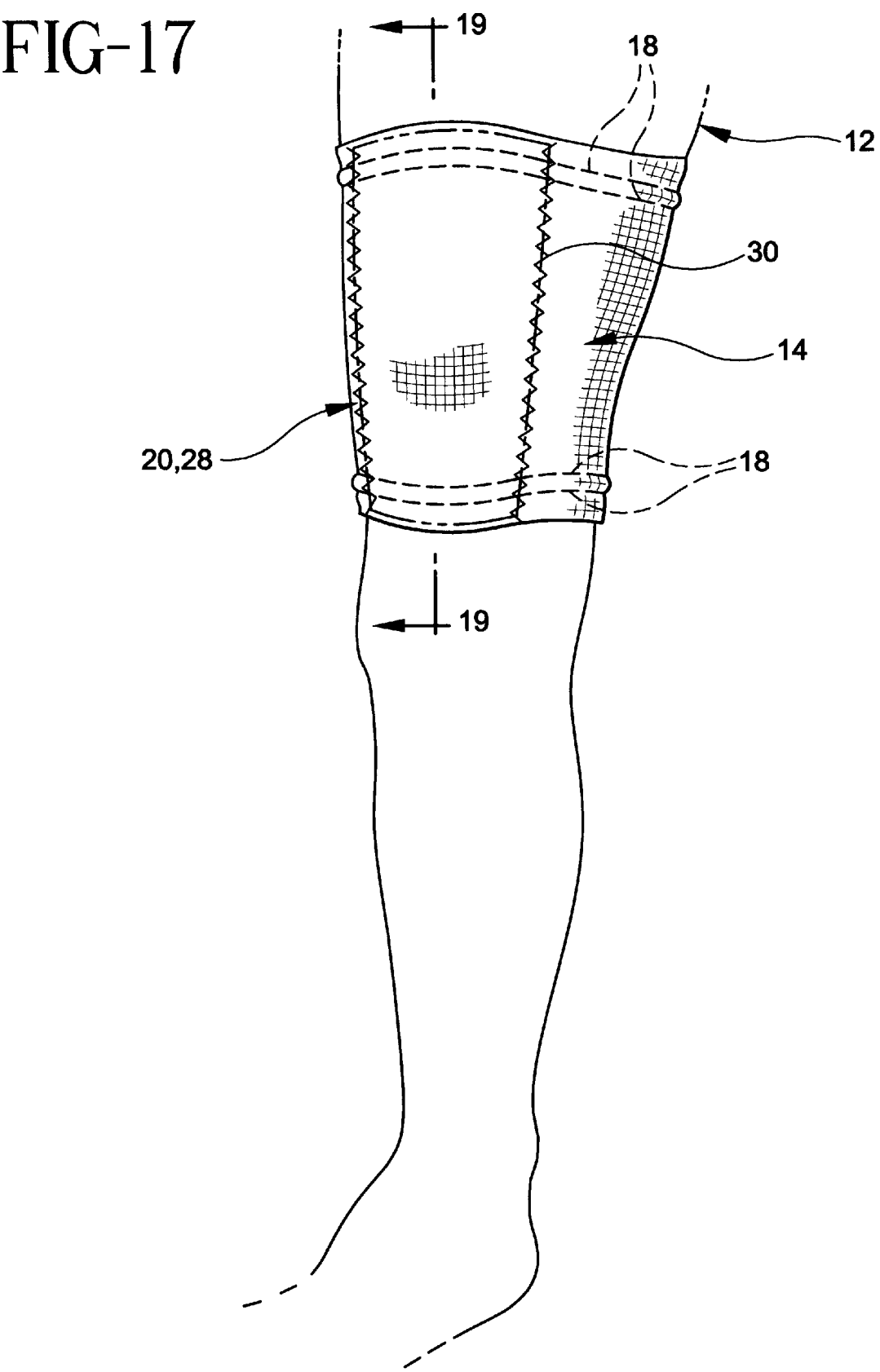
FIGS. 17 and 18 are views in perspective and a flattened front plan, respectively, of an elastic thigh support according to the present invention.
Figure 18:
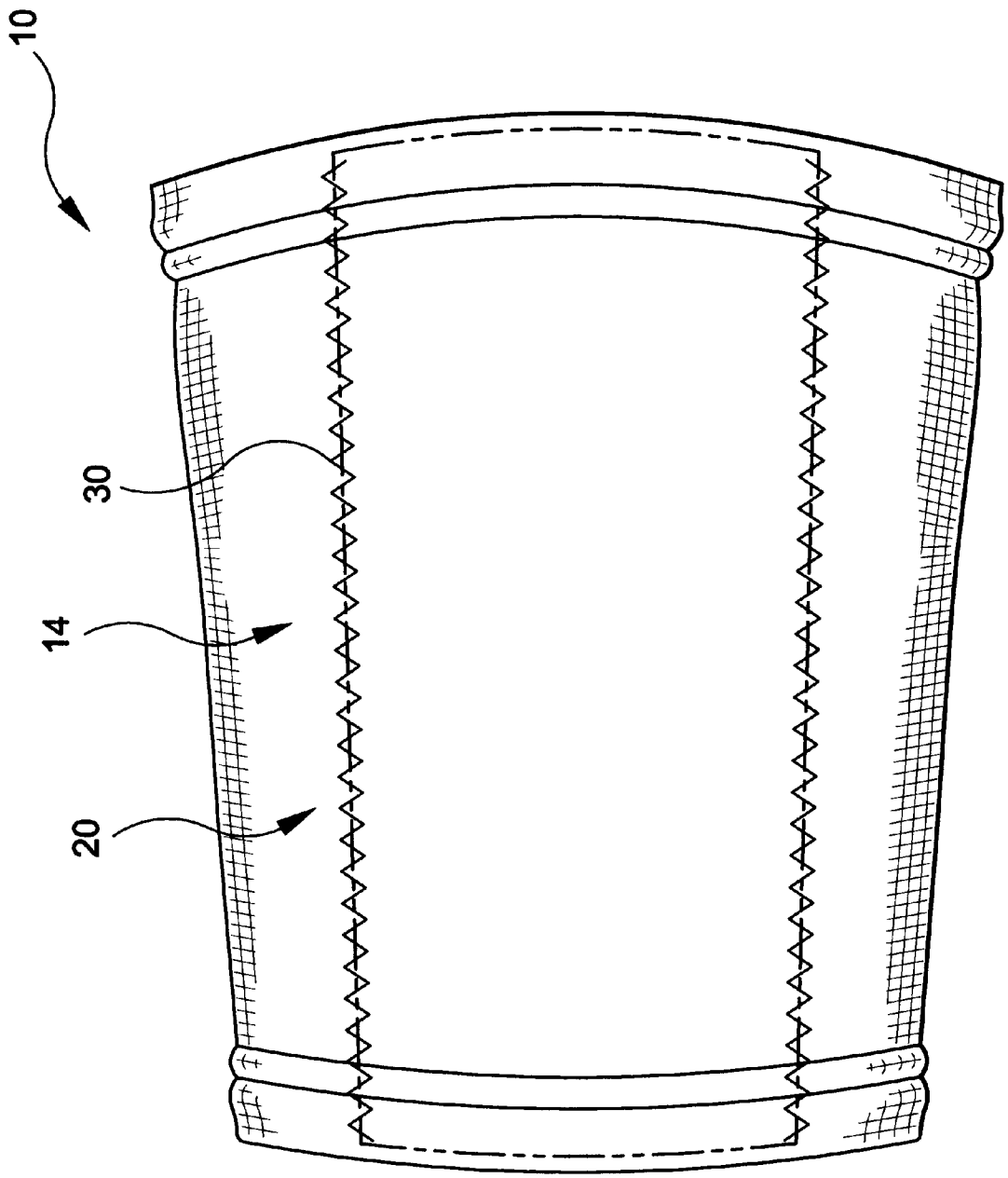

FIGS. 17–19 show a support 10 adapted for use on a thigh. The sleeve 14 tapers to a lower, narrower end near the knee. The patch 20 is a generally parallel-sided strip that extends generally vertically when worn by a person who is standing, as shown in FIG. 17. The patch 20 extends substantially the full height of the sleeve, and is wide enough to cover a selected major muscle or tendon group that extends along the thigh. The patch is shown positioned over the front of the thigh to the quadracep extensor muscles at this location. It can be rotated to the rear of the thigh to treat a hamstring muscle pull, or a variety of other injuries or conditions in the thigh. The liner 26 is continuous, without openings 33.

There has been described an elastic support for joints and other body parts that provides both mechanical support and strategically positioned therapeutic heating where the heating is generated by retaining body heat, not by thermal packs, electrical heating coils, or other external sources of thermal energy. The support provides these advantages while controlling the adverse effects of excessive moisture, chafing, and bite. The support is highly flexible, lightweight, and compact. It also provides an enhanced degree of protection against injury or injury aggravation induced by external blows as compared to conventional sleeve-type supports. The support can be worn during physical activity and for extended periods of time without a level of discomfort that forces the wearer to remove the support prematurely. It uses commonly available materials and construction techniques. It uses reduced quantities of neoprene, or an equivalent material, as compared to supports made entirely with a heat-retaining layer; it therefore offers a reduced cost of materials. The support is rugged, durable, washable, and easily foldable to pack for travel or for point-of-sale packaging.

While this invention has been described with reference to its preferred embodiments, it will be understood that various modifications and alterations will occur to those skilled in the art from the foregoing detailed description and the accompanying drawings. For example, while the invention has been described with reference to supports for certain body parts, the features of this invention described herein can be readily adapted to produce for other body parts such as the lower back, calf, shoulder, and foot. Further, while the patch has been described with a single liner 26, it can be formed from a material with two layers of stretch fabric which cover a heat-retaining layer, with or without holes 33 in one or both fabric layers, and with a variety of attachment mechanisms. However, because the present patch 20 is used in combination with the elastic sleeve 14, such a third fabric layer, and its continuous adherence to a heat-retaining layer, are not necessary. The patch can even be a single heat-retaining layer with no liner, but this arrangement presents significant moisture and over-heating problems when worn over a layer of clothing or the like. The holes 32 and 33 can assume other forms, such as elongated slots or ovals, provided that sufficient air circulation is maintained and the structural integrity of the patch is not significantly degraded. The liner 26 has been shown as being co-extensive with the layer 24, but it can cover less then all of the layer 24, or it can extend beyond it to form a complete or partial lining of the entire inner surface of the sleeve 14, as well as the entire layer 24. There are clear, comfort, durability, and cost disadvantages associated with these modifications. Also, while the stretch fabrics have been described as preferably a woven nylon, they can be formed of other materials with like properties and formed of knitted as well as woven fabrics. However, there may be disadvantageous trade-offs in stretch, resilient force, durability, washability, odor retention or other factors well known to those skilled in the art. These and other such modifications and variations are intended to fall within the scope of the appended claims.

What is claimed is:

1. An elastic support for a body part where the support provides strategically placed therapeutic heat treatment to a selected portion of the body part, said elastic support comprising:

a main elastic support member formed of a multi-directional stretch fabric that surrounds the body part in a stretched condition that produces a compression on the body part when in use;

a patch of a flexible laminate having a layer that retains a body heat, said patch being sized, shaped and located on said main elastic support member at the selected portion to provide the therapeutic treatment only to the selected body portion and located on an inner surface of said main elastic support member;

attachment means for securing said patch to said main elastic support member; a plurality of holes that extend through said layer that retains body heat to control moisture at the selected body portion;

a liner located between the patch and said selected body portion when in use having a plurality of holes aligned with said plurality of holes in said layer that retains body heat, wherein said liner is generally coextensive with said patch and is secured to at least one of said patch and said main elastic support member:

a laminating means for securing said liner to said patch; and wherein the body part is a knee and wherein said patch is (i) generally diamond shaped. (ii) centered over the knee cap when said main elastic support member is in use, and (iii) extends vertically and horizontally to cover the knee cap and immediately adjacent body tissue.

2. An elastic support for a body part where the support provides strategically placed therapeutic heat treatment to a selected portion of the body part, said elastic support comprising:

a main elastic support member formed of a multi-directional stretch fabric that surrounds the body part in a stretched condition that produces a compression on the body part when in use:

a patch of a flexible laminate having a layer that retains a body heat, said patch being sized, shaped and located on said main elastic support member at the selected portion to provide the therapeutic treatment only to the selected body portion and located on an inner surface of said main elastic support member:

attachment means, for securing said patch to said main elastic support member; a plurality of holes that extend through said layer that retains body heat to control moisture at the selected body portion;

a liner located between the patch and the selected body when in use portion when in use having a plurality of holes aligned with said plurality of holes in said layer that retains body heat, wherein said liner is generally coextensive with said patch and is secured to at least one of said patch and said main elastic support member;

a laminating means for securing said liner to said patch; and wherein the body part is an elbow and wherein said patch is (i) generally diamond shaped, (ii) located centered over the elbow when the elastic support member is in use, and (iii) extends vertically and horizontally to cover the elbow and immediately adjacent tissue.

3. An elastic support for a body part where the support provides strategically placed therapeutic heat treatment of the body part, said elastic support comprising:

a main elastic support member formed of a multi-directional stretch fabric that surrounds the body part in a stretched condition that produces a compression on the body part when in use;

a patch of a flexible laminate having a layer that retains a body heat, said patch being sized, shaped and located on said main elastic support member at the selected portion to provide the therapeutic treatment only to the selected body portion and located on an inner surface of said main elastic support member;

attachment means for securing said patch to said main elastic support member;

a plurality of holes that extend through said layer that retains body heat to control moisture at the selected body portion a liner located between said patch and the selected body portion when in use having a plurality of holes aligned with said plurality of holes in said layer that retains body heat, wherein said liner is generally coextensive with said patch and is secured to at least one of said patch and said main elastic support member;

a laminating means for securing said liner to said patch; and wherein the body part is an ankle and wherein said patch is a strip that circles the ankle at the rear and above the heel and is rounded at its two ends at the front of the ankle.

4. The therapeutic support as in any of claims 1, 3 or 3, wherein said attachment means and said laminating means both comprise a common stitching along the periphery of said patch and said liner.

5. The therapeutic support of claim 4 wherein said laminating means further includes spot adhering of said liner to said patch to maintain them in an overlapping relationship during said peripheral stitching.

6. The therapeutic support of claim any of claims 1, 2 or 3 wherein said liner is formed of a fabric that wicks perspiration.

7. The therapeutic support as in any of claims 1, 2 or 3 wherein said patch is formed of a closed cell foam.

8. The therapeutic support as in any of claims 1, 2 or 3 wherein said elastic support member is a generally tubular sleeve.

9. The therapeutic support of claim 8 wherein said sleeve has an interior opening sized and located to accommodate a flexure of said body part.

10. The therapeutic support as in any of claims 1, 2 or 3 wherein said attachment and lamination means are each selected from the group consisting of (i) spot gluing and edge stitching, (ii) edge stitching, (iii) stitching (iv) continuous adhesion, (v) heat lamination, (vi) loop and hook attachment, and (vii) any combination of (i)–(vi).

* * * * *